(12) United States Patent
Creaghan, Jr.

(10) Patent No.: US 6,923,762 B1
(45) Date of Patent: Aug. 2, 2005

(54) VENOSCOPE APPARATUS

(76) Inventor: Frank C. Creaghan, Jr., P.O. Box 52703, Lafayette, LA (US) 70505-2703

( * ) Notice: Subject to any disclaimer, the term of this patent is extended or adjusted under 35 U.S.C. 154(b) by 262 days.

(21) Appl. No.: 10/278,301

(22) Filed: Oct. 22, 2002

Related U.S. Application Data

(60) Provisional application No. 60/334,821, filed on Nov. 1, 2001.

(51) Int. Cl.[7] ............................................... A61B 1/06
(52) U.S. Cl. ..................................... 600/249; 362/231
(58) Field of Search .............................. 600/249, 160, 600/178, 179, 180, 199, 245; 362/231, 800; 433/29, 215

(56) References Cited

U.S. PATENT DOCUMENTS

| | | | |
|---|---|---|---|
| 2,161,688 A * | 6/1939 | Schwartz | 600/249 |
| 3,527,932 A * | 9/1970 | Thomas | 600/249 |
| 4,112,923 A * | 9/1978 | Tomecek | 600/11 |
| 4,286,602 A * | 9/1981 | Guy | 600/476 |
| 4,312,357 A * | 1/1982 | Andersson et al. | 600/473 |
| 4,619,249 A * | 10/1986 | Landry | 600/245 |
| 4,650,327 A * | 3/1987 | Ogi | 356/243.1 |
| 4,830,014 A * | 5/1989 | Goodman et al. | 600/310 |
| 4,867,138 A * | 9/1989 | Kubota et al. | 600/107 |
| RE33,234 E | 6/1990 | Landry | |
| 4,932,776 A * | 6/1990 | Dowling et al. | 356/71 |
| 5,187,377 A * | 2/1993 | Katoh | 257/89 |
| 5,337,744 A * | 8/1994 | Branigan | 600/407 |
| D362,910 S | 10/1995 | Creaghan | |
| 5,683,350 A * | 11/1997 | Paul et al. | 600/249 |
| 5,851,063 A * | 12/1998 | Doughty et al. | 362/231 |
| 6,084,250 A * | 7/2000 | Justel et al. | 257/89 |
| 6,178,340 B1 * | 1/2001 | Svetliza | 600/319 |
| 6,230,046 B1 * | 5/2001 | Crane et al. | 600/476 |
| 6,272,269 B1 * | 8/2001 | Naum | 385/43 |
| 6,337,536 B1 * | 1/2002 | Matsubara et al. | 313/498 |
| 6,351,069 B1 * | 2/2002 | Lowery et al. | 313/512 |
| 6,357,893 B1 * | 3/2002 | Belliveau | 362/285 |
| 6,478,447 B2 * | 11/2002 | Yen | 362/231 |
| 6,527,419 B1 * | 3/2003 | Galli | 362/308 |

FOREIGN PATENT DOCUMENTS

| | | | | |
|---|---|---|---|---|
| JP | 2-172473 | * | 7/1990 | A61M 5/00 |
| JP | 2-174854 | * | 7/1990 | A61M 5/00 |
| WO | WO 99/29231 | * | 6/1999 | A61B 5/00 |

* cited by examiner

*Primary Examiner*—Eduardo C. Robert
*Assistant Examiner*—David Comstock
(74) *Attorney, Agent, or Firm*—Garvey, Smith, Nehrbass & Doody, L.L.C.; Gregory C. Smith

(57) ABSTRACT

An improved instrument for viewing subcutaneous venous structure, known as a VENOSCOPE, which includes a clamshell housing, having a first fixed arm extending therefrom, and a second movable arm captured by upper and lower portions of the housing; a first high intensity plurality of white and red LEDs positioned at the end of the first arm, and a second high intensity plurality of high intensity red and white LED positioned at the end of the second arm, and a battery positioned within the housing for selectively provided electrical energy to the red and white LEDs, so that a more defined and intensely illuminated field of visualization between structures below the skin and the surrounding subcutaneous tissue is defined. Additional embodiments include a tube or handle connected to a head having multiple arms or a single arm with multiple LEDs.

15 Claims, 6 Drawing Sheets

VENOSCOPE APPARATUS

CROSS-REFERENCE TO RELATED APPLICATIONS

Priority of U.S. Provisional Patent Application Ser. No. 60/334,821, filed Nov. 1, 2001, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The apparatus of the present invention relates to instruments for viewing subcutaneous venous structures.

2. General Background of the Invention

In the medical field, the task of locating venous structures, such as peripheral veins, is a difficult task. There have been attempts to make the task less difficult. One such device, which is currently under U.S. Pat. No. RE 33,234, is an instrument which directs a pair of light beams through the ends of a pair of arms pressed against the skin to produce an illuminated field beneath the skin, where peripheral veins can be visualized and located. The preferred lighting means in this patent utilized a white halogen lights with fiber optics. The drawback in this device was the fact that the lights at that state of the art could not produce the necessary candle power to properly illuminate the area.

BRIEF SUMMARY OF THE INVENTION

The improved apparatus of the present invention solves the problems in the art in a simple manner. What is provided is an improved instrument for viewing subcutaneous venous structure, known as a VENOSCOPE, which includes a principal body, having a first fixed arm extending therefrom, and a second movable arm captured by upper and lower body portions; a plurality of ultra bright red and white LEDs positioned at the end of the first arm, and a second plurality of ultra bright red and white LEDs positioned at the end of the second arm. Preferably the red LEDs would have a wavelength of 700 to 430 nanometers; and the white LEDs having a wavelength range of 460 to 555 nanometers; and a battery positioned within the body for selectively providing electrical energy to the plurality of red and white LEDs, so that a more defined and intensely illuminated field of visualization of the structures below the skin and the surrounding subcutaneous tissue can be defined.

Therefore, it is a principal object of the present invention to provide an improved VENOSCOPE apparatus, utilizing a combination of ultra bright red and white LED's to more effectively locate subcutaneous structures, such as veins, below the skin;

It is a further object of the present invention to provide a light-weight, compact, battery powered VENOSCOPE that improves the visual field of structures below the skin with the use of a combination of ultra bright LEDs;

It is a further object of the present invention to provided an improved VENOSCOPE apparatus, which through the use of a combination of enhanced red and white light fields provides a visual field that is more greatly enhanced and improves the task of locating structures below the skin;

It is a further object of the present invention to provide an improved VENOSCOPE apparatus, where the red and white LEDs have differing and varying wavelengths so as to achieve a greater penetration of the subcutaneous tissue and achieve a greater contrast with the blood vein;

It is a further object of the present invention to provide an improved VENOSCOPE apparatus, where the red LEDs provide deeper penetration into the subcutaneous tissue and the white LEDs provides contrast between the subcutaneous tissue in order to present the blood vein as a dark line within the tissue between the arms of the device.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
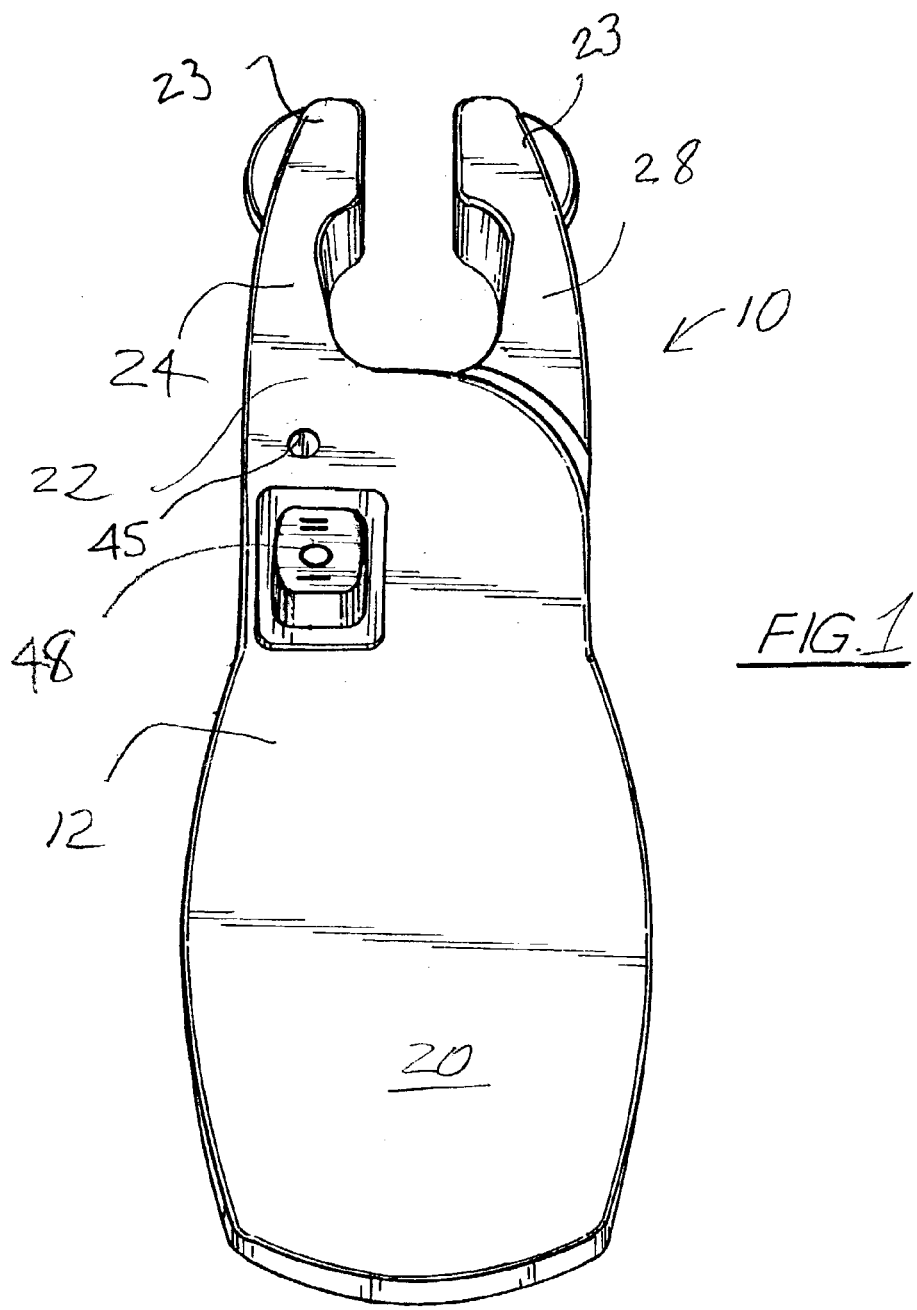
FIG. 1 is an overall top view of the preferred embodiment of the apparatus of the present invention.
Figure 2:
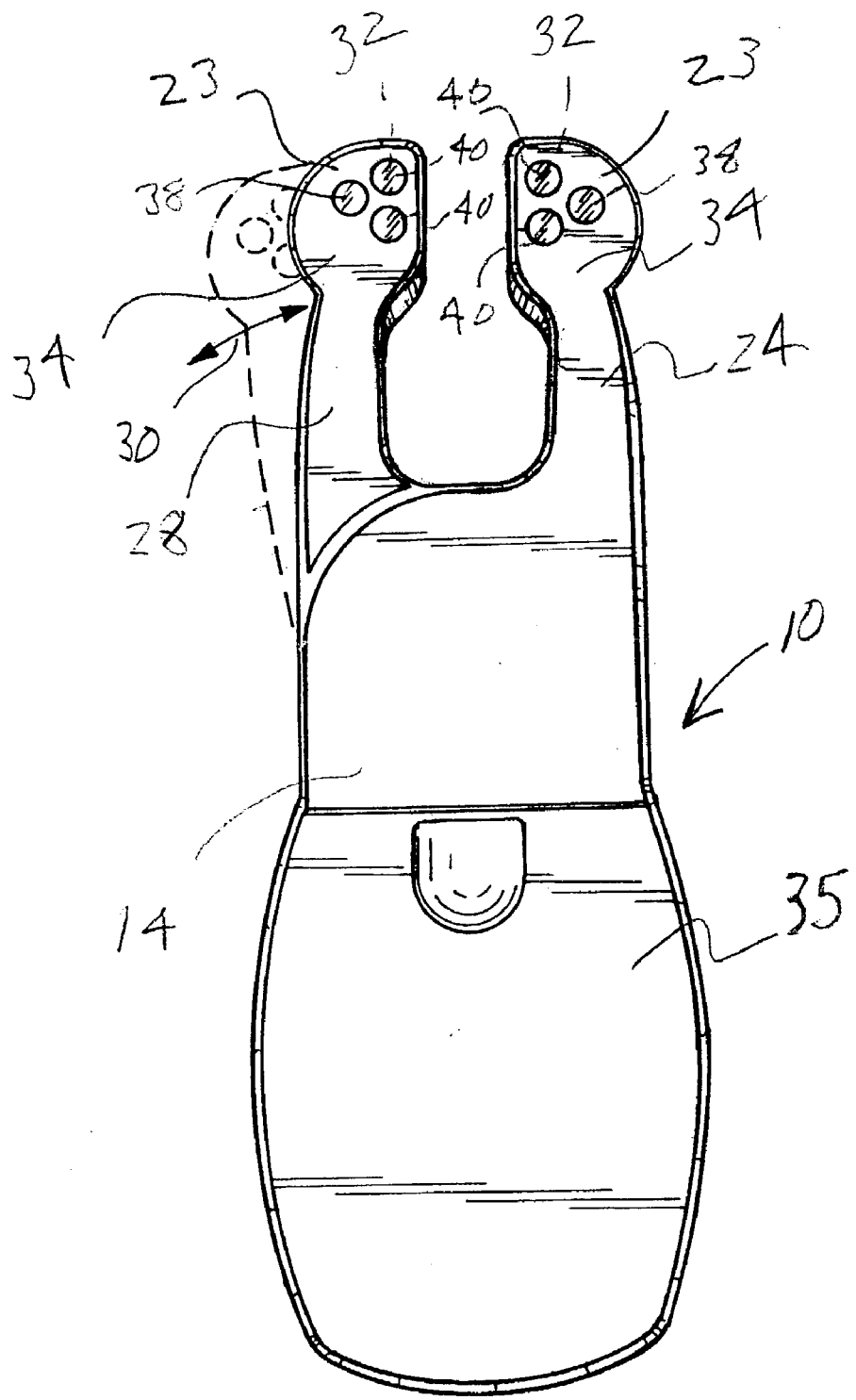
FIG. 2 is an overall underside view of the preferred embodiment of the apparatus of the present invention.
Figure 3:
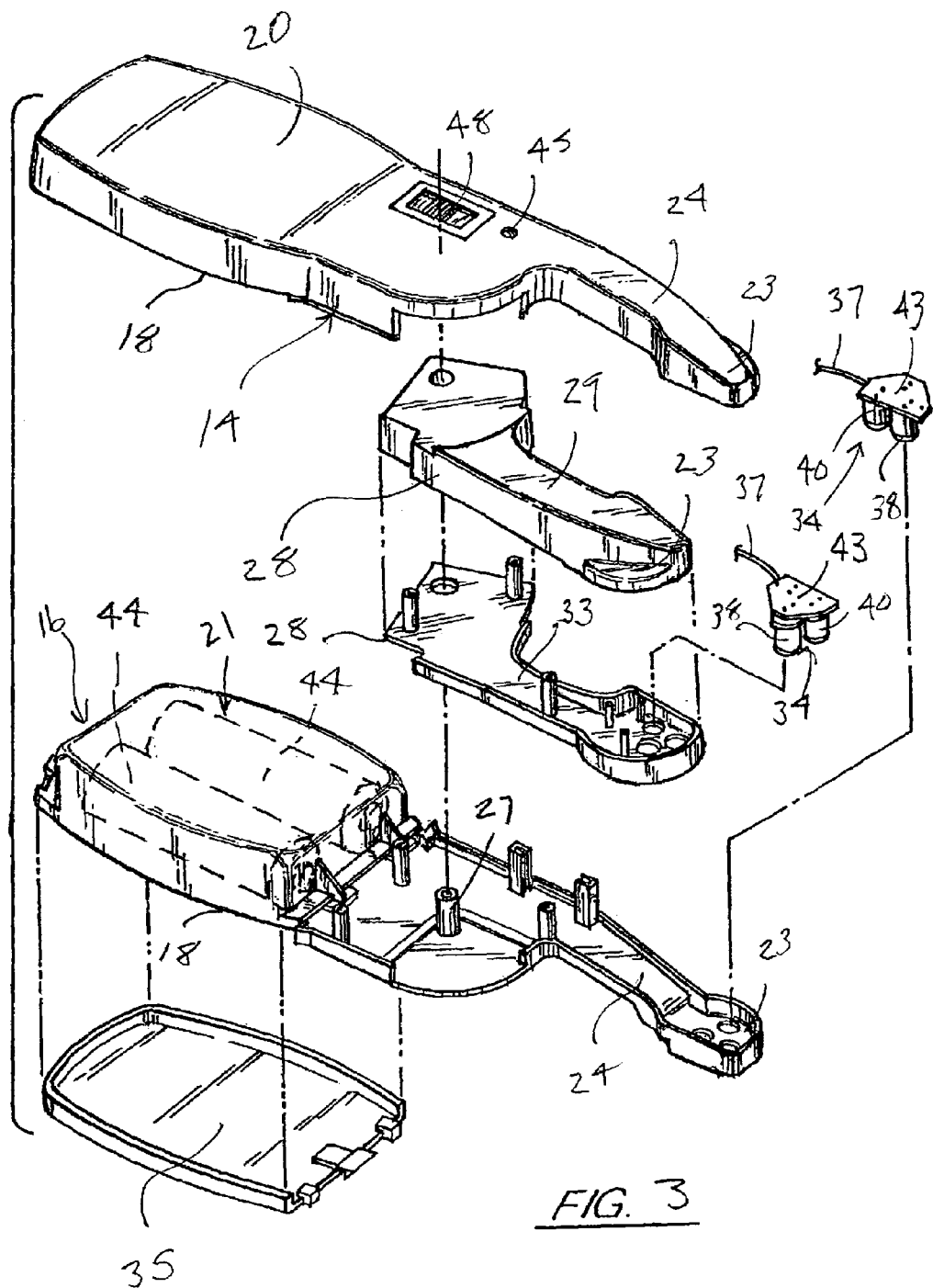
FIG. 3 is an exploded view of the apparatus of the present invention.

FIGS. 1 through 5 illustrate the preferred embodiment of the improved VENOSCOPE apparatus 10 of the present invention. VENOSCOPE is a trademark owned by Venoscope, L.L.C. As illustrated in FIGS. 1 through 3, apparatus 10 in overall view provides a principal body 12, having an upper body portion 14, and a lower body portion 16, the two body portions 14, 16 secured along a common edge 18 to define the complete principal body 12 when portions 14, 16 are assembled. As further illustrated, a first rear end of the housing 12 provides an area 20 for grasping the apparatus, while in use, and the second end 22, terminates in a first fixed arm portion 24. Upper body portion 14 further provides a means internal to the body portion for allowing a second moveable arm portion 28 to be moveably secured between housings 14, 16, for allowing movement of the arm 28 in the direction of arrow 30 in FIG. 2.

Figure 4:
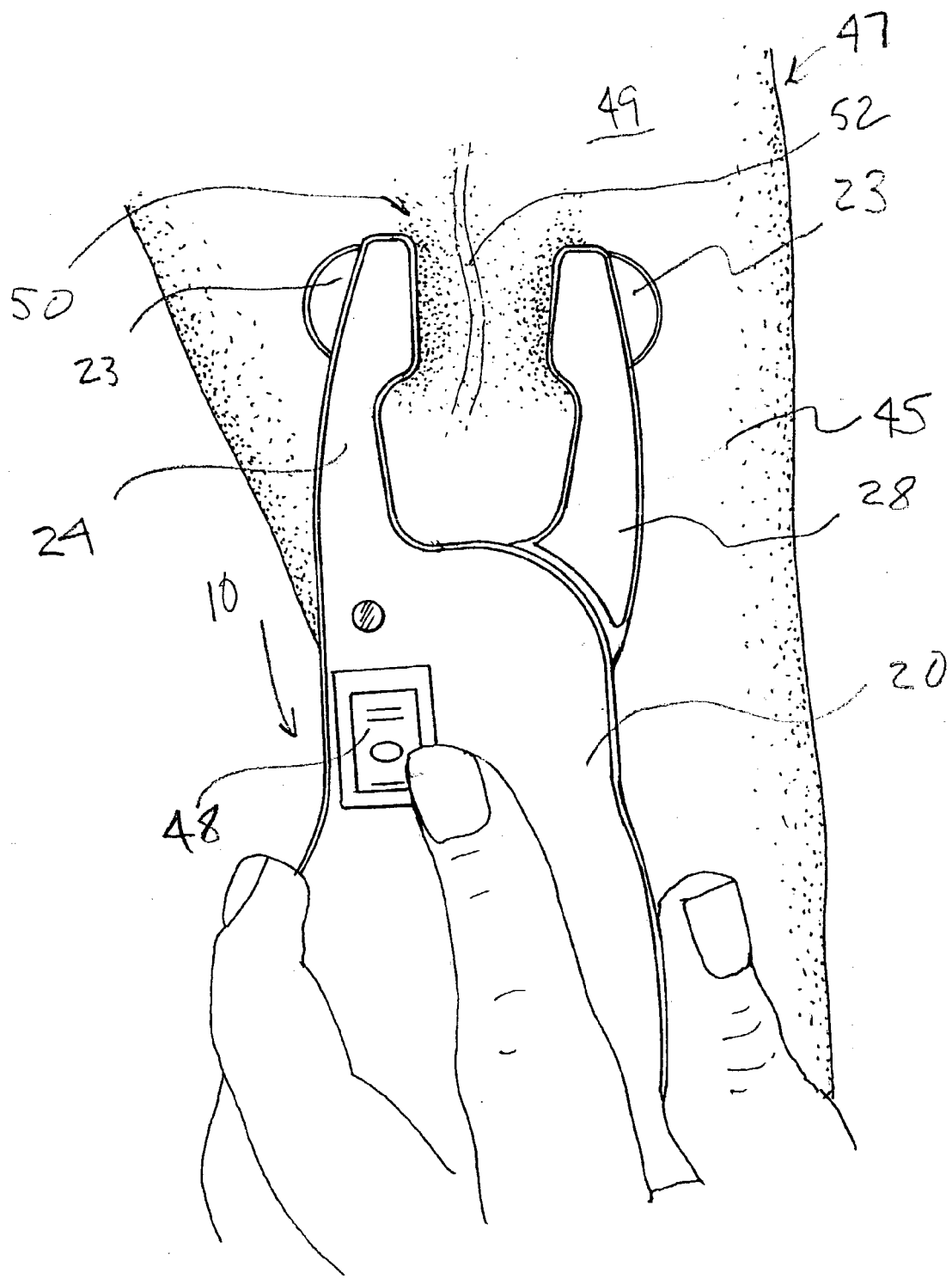
FIG. 4 is a top view of the apparatus of the present invention in place on a human limb detecting a vein.

As seen further in FIG. 2, the distal ends 23 of the arms 24, 28 include a plurality of openings 32, each of which may be one or more openings, which would allow light to travel out of, emanating from a light source, preferably high intensity LEDs, within each end 23 of each of the arms 24, 28. Preferably, each end 23 would have a plurality of three openings 32, two of which would emanate light from two white LEDs and one opening emanating red light from a single red LED. This combination allows the red LED to penetrate deeper and the whites to provide the contrast between the subcutaneous tissue and the veins which absorb light and appear as a dark line. This will be more fully explained in later figures. As seen further in FIG. 2, the underside of apparatus 10 includes a plate 35 which is removable for replacing batteries 44 within the apparatus 10. Preferably, batteries 44 would be a plurality of AA batteries 44, and indicator light 45 (FIG. 1) would indicate when the batteries 44 are low in power. The power from the batteries 44 to the light source, or LEDs, would be controlled by a manual switch 48 as seen in FIGS. 1 and 4. In the preferred embodiment manual switch 48 would include a first HIGH position, wherein the LEDs are operational at 100%; a second LOW position, wherein the operation of the LEDs are reduced in power approximately 30%; and a third OFF position.

In FIG. 3, the apparatus is illustrated in exploded view, showing the upper and lower housings 14, 16. As seen the upper housing 14 includes the upper portion of the area 20 having the upper portion of the fixed arm 24. There is further seen the lower housing portion 16, including an area 21, which as seen is configured to house several batteries 44. There is provided a removable face plate 35 for allowing the batteries to be secured therein. Further, FIG. 3 illustrates the moveable arm 28, which also has an upper and lower portions 29, 33 which would fit together to form the composite arm 28. The composite arm 28 would rotate around peg member 27, when the upper housing 14 and lower housing 16 are engaged to one another and assembled. Further, as illustrated in FIG. 3, there appears light means 34, which comprise a first red LED 38 and a pair of white LEDs 40. The LEDs 38, 40 are an array of red and white LEDs, which are raised on a circuit board 43 to be inserted into the distal end 23 of each arm 24, 28 and positioned flush with the patient's skin when the apparatus is used in its completed form, as will be discussed in FIGS. 4 and 5. The LEDs 38, 40, affixed to the circuit board 43 in each arm, with wires 37 extending between the two sets of LEDs 38, 40 a plurality of batteries 44.

The LEDs 38, 40 provide the improved VENOSCOPE apparatus using a combination of ultra bright red and white LED's to more effectively locate subcutaneous structures, such as veins, below the skin. The LEDs 38, 40 utilized in the present invention may be those of the type sold by Marktech Optoelectronics, which are referred to as high intensity red LEDs and white LEDs. The use of these high intensity LEDs 38, 40 improves the visual field of structures below the skin with the use of a combination of the ultra bright LEDs. The combination of enhanced red and white light fields provides a visual field that is more greatly enhanced and improves the task of locating structures below the skin. This is accomplished by the fact that the red and white LEDs have differing and varying wavelengths so as to achieve a greater penetration of the subcutaneous tissue and achieve a greater contrast with the blood vein. In effect, the red LEDs provide deeper penetration into the subcutaneous tissue and the white LEDs provides contrast between the subcutaneous tissue in order to present the blood vein as a dark line within the tissue between the arms of the device. In the preferred embodiment the red LEDs would have a wavelength of 700 to 430 nanometers; and the white LEDs having a wavelength range of 460 to 555 nanometers. This differing wavelength between the red and white LEDs would enhance the contrast between the vein and the surrounding subcutaneous tissue around the vein.

Figure 5:
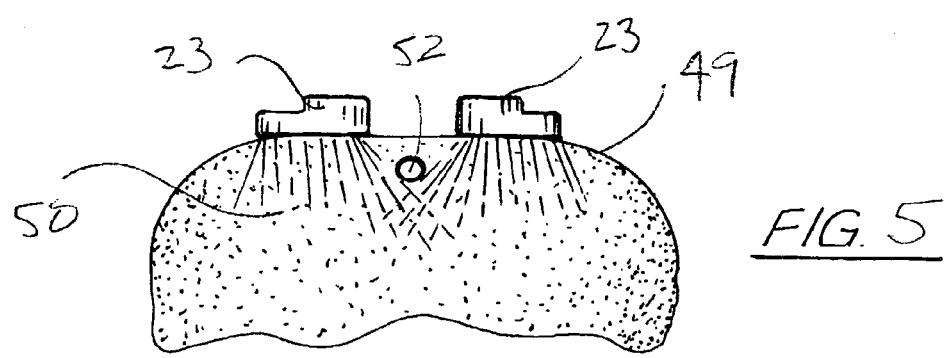
FIG. 5 is an end view of the apparatus of the present invention illuminating the vein depicted in FIG. 4.

This is clearly illustrated in FIGS. 4 and 5. As seen in FIG. 4, the apparatus 10 has been placed on the forearm 45 of a patient 47, with the openings 32 pressed against the skin 49. Two openings in each arm 24, 28 would be provided with a white LED 40, while one opening 32 would be provided with a single red LED 38, for the reasons explained earlier. The switch 48 on the apparatus 10 is placed to the ON position, thus energizing the red and white LEDs 38, 40. The 430 to 700 nm wavelength of the red LED 38 would provide the deeper penetration into the subcutaneous tissue 50 as illustrated. The preferable red LED 38 wavelength would be around 623 nm. The 460 to 555 nm wavelength of the white LED 40 would present the vein 52 as a dark line beneath the skin in the area between the two arms 24, 28 of the apparatus. The preferable white LED 40 wavelength would be around 500 nm. This would allow the doctor or clinician to locate the vein 52 more readily in order to provide the necessary treatment. Again, this combination of red and white LED groups 38, 40 would provided a greatly enhanced field of illumination below the skin, and would greatly enhance the functioning of the apparatus.

It is foreseen, however, that although the preferred embodiment teaches the use of two white LEDs and a single red LED in each arm, perhaps one arm of the apparatus may contain only white LEDs and the second arm contain only red LEDs, and may still function within acceptable limits. It is also foreseen that in the future other colors may be derived which produce the necessary contrast between the subcutaneous tissue and the structures therein, other than red and white as are utilized presently. Additionally, should it be found that the wavelength of the LEDs increase or decrease beyond the limits discussed herein, and these limits are capable of producing the necessary contrast between the subcutaneous tissue and the structures therein, such modifications are considered to be part of the present invention.

Figures 6A, 6B:
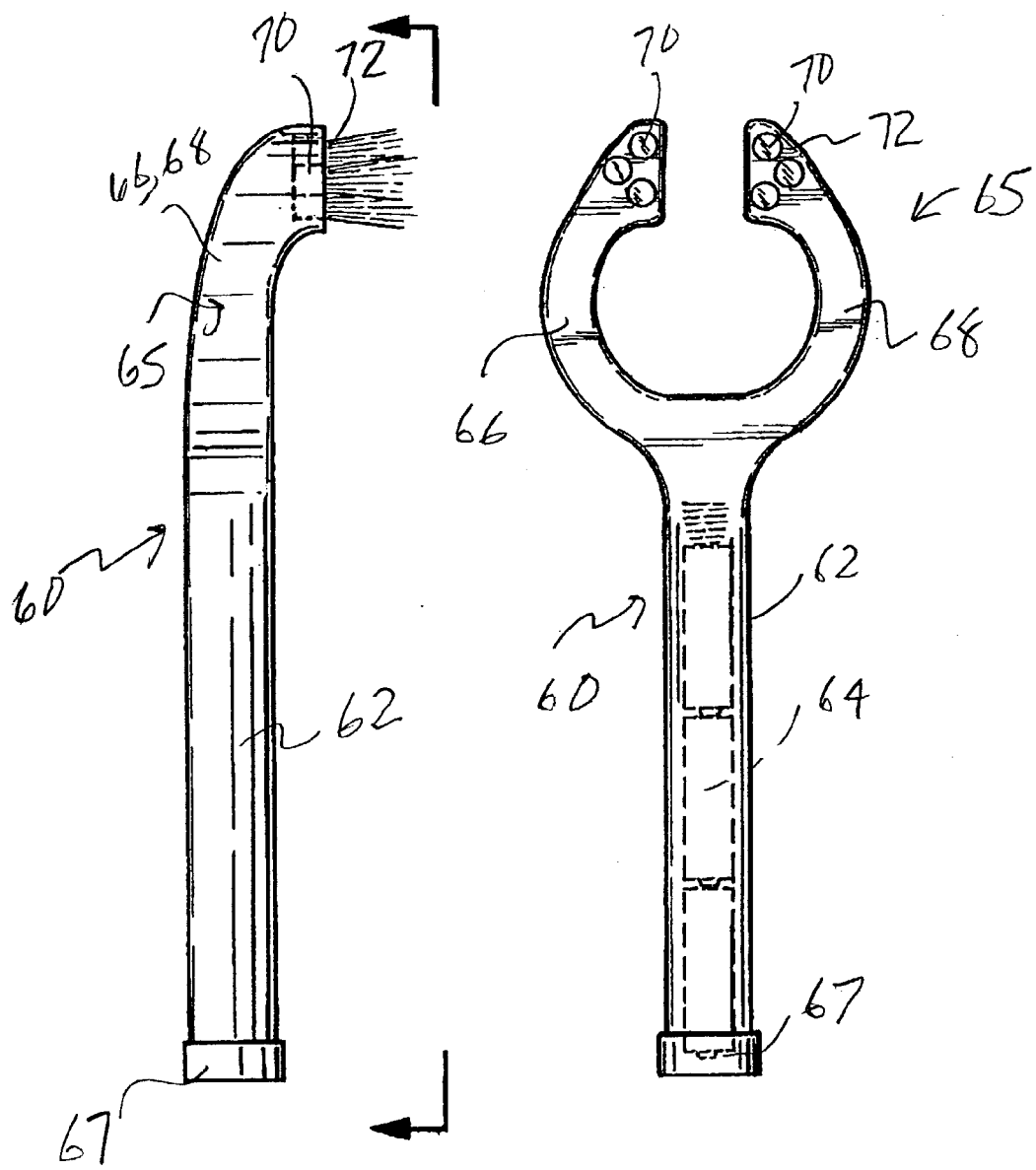
FIGS. 6A and 6B illustrate a first additional embodiments of the present invention.

FIGS. 6A and 6B illustrates a first additional embodiment of the apparatus referenced by the numeral 60. As illustrated in underside and side views, apparatus 60 would comprise an elongated handle member 62, having a hollow interior for housing a plurality of batteries, preferably double A batteries 64.

The batteries 64 would be inserted into handle member 62 by removing end cap 67. The handle or tube 62 would terminate in head portion 65, which includes a pair of arm 66, 68, one of which may be moveable relative to the second arm, although both arms 66, 68 may be fixed on the head 65. Each arm 66, 68 would include a plurality of LEDs 70, preferably 3 LEDs, fixed to a face 72 of end of each arm, which would be pressed against a person's skin to carry out the function. The LEDs would be similar in color and arrangement as was discussed with the principal embodiment. Of course, the batteries 64 would provide power to the LEDs 70, when the apparatus is turned on, either through a manual switch on the apparatus or when the tube 62 is engaged to the head portion 65.

Figure 7A:
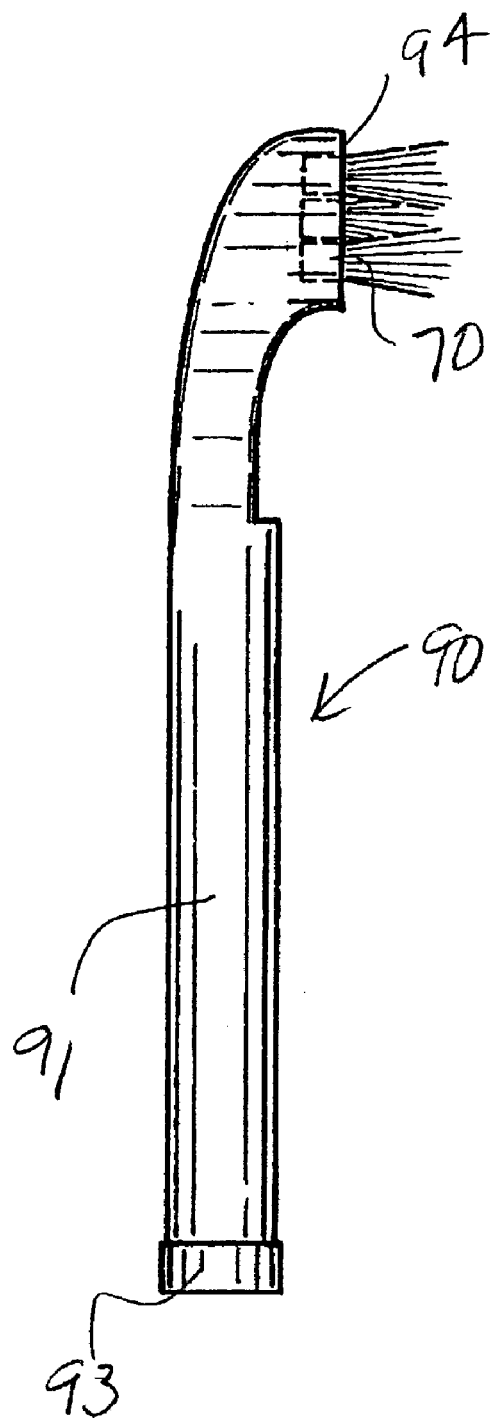
FIGS. 7A and 7B illustrate a second additional embodiments of the present invention.
Figure 7B:
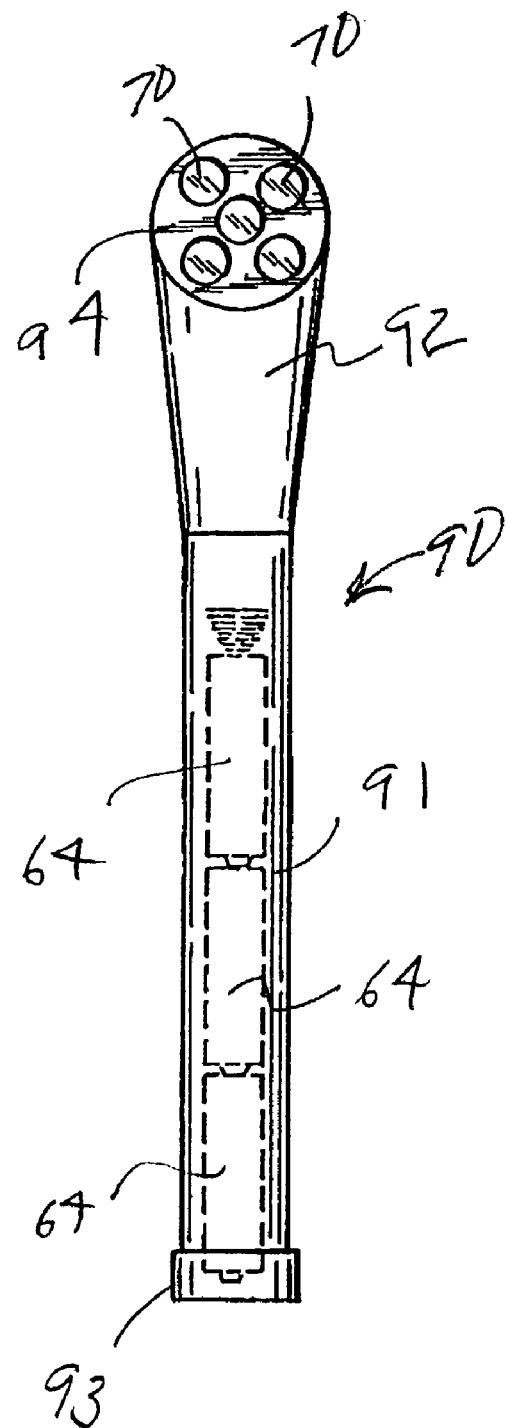

In FIGS. 7A and 7B another embodiment of the apparatus, referenced by the numeral 90. Apparatus 90 comprises a single arm or tube 91, with a hollow interior for housing a plurality of AA batteries 64, as with the embodiment discussed in FIGS. 6A and 6B. Likewise, the batteries 64 would be inserted into arm or tube member 91 by removing end cap 93. The tube 91 would terminate in a single fixed arm 92, which would include a face 94, having a plurality of LEDs 70, with the LEDs numbering preferably five, in the combination of red and white LEDs. The LED array on the face 94 would shine at a 90 degree angle relative to the arm 91, when the apparatus 90 is pressed against the skin of a patient for use.

Since it is foreseen that the improved VENOSCOPE apparatus 10, or embodiments 60 and 90, would be sold as a possible "throwaway" item after use, the apparatus housed may be marketed within a plastic clamshell packaging, having an instruction card, or the like for instructing on how to use the apparatus. apparatus 10
principal body 12
upper body portion 14
lower body portion 16
common edge 18
area 20
second end 22
distal ends 23
first fixed arm portion 24
peg 27
moveable arm 28
upper portion 29
arrow 30
openings 32
lower portion 33
light means 34
face plate 35
wires 37
red LED 38
white LED 40
circuit board 43
batteries 44
forearm 45
patient 47
manual switch 48
skin 49
subcutaneous tissue 50
vein 52
apparatus 60
handle member 62
batteries 64
head portion 65
end cap 67
arms 66, 68
LEDs 70
face 72
apparatus 90
arm or tube 91
fixed arm 92
end cap 93
face 94

The foregoing embodiments are presented by way of example only; the scope of the present invention is to be limited only by the following claims.

What is claimed is:

1. An improved apparatus for viewing subcutaneous structures comprising:
   a. a principal body portion, graspable by the hand;
   b. a first arm fixed on a first end of the body portion;
   c. a second arm, extending from the first end of the body portion, and moveable in relation to the fixed arm;
   d. light members positioned on the end of each arm member, comprising a combination of high intensity red and white LEDs to provide enhanced visualization of subcutaneous structures when the LEDs are pressed against the skin; and
   e. power means to provide energy for illuminating the LEDs.

2. The apparatus in claim 1, wherein the body portion comprises first and second portions engaged along a common edge, and capturing an end portion of the moveable arm portion.

3. The apparatus in claim 1, wherein the ultra bright red LEDs provide a wavelength in the range of 430 to 700 nanometers (nm) of emission power each.

4. The apparatus in claim 1, wherein the ultra bright white LEDs provide a wavelength in the range of 460 to 555 nanometers (nm) of emission power each.

5. The apparatus in claim 1, wherein the apparatus may be packaged for selling as a disposable unit after use.

6. The apparatus in claim 1, wherein the power means comprises a battery pack having sufficient energy to provide illumination to the ultra bright LEDs.

7. An improved apparatus for viewing subcutaneous structures, such as veins, comprising:
   a. a principal body portion;
   b. first and second arms fixed on a first end of the body portion, defining a viewing space therebetween;
   c. at least one red LED having a wavelength in the range of 430 to 700 nanometers (nm) positioned at an end of a first arm member;
   d. at least one white LED having a wavelength in the range of 460 to 555 nanometers (nm) positioned at an end of a second arm member;
   e. power means to provide energy for illuminating the LEDs;
   f. the combination of red and white LEDs used substantially simultaneously providing enhanced visualization of the vein located subcutaneously, when the LEDs are pressed against the skin and illuminated.

8. The apparatus in claim 7, wherein the red LED would possess a wavelength of around 623 nm.

9. The apparatus in claim 7, wherein the white LED would possess a wavelength of around 500 nm.

10. The apparatus in claim 7, wherein the second arm member would be moveable in relation to the first arm member.

11. The apparatus in claim 7, wherein there would be included a plurality of red and white LEDs in the first and second arm members.

12. An improved apparatus for viewing subcutaneous structures, such as veins, comprising:
   a. a principal body portion;
   b. first and second arms positioned on the body portion, defining a viewing space therebetween;
   c. red and white high intensity LEDs positioned in the arm members of differing wavelengths so that when illuminated together against skin provide a contrast between structures, such as veins, beneath the skin and the surrounded subcutaneous tissue, so that the structures can be more readily located and identified; and
   d. means for providing electrical power to illuminate the plurality of LEDs.

13. The apparatus in claim 12, wherein at least one red LED has a wavelength in the range of 430 to 700 nanometers (nm).

14. The apparatus in claim 12, wherein at least one white LED has a wavelength in the range of 460 to 555 nanometers (nm).

15. The apparatus in claim 12, further comprising a manual switch which would include "high" and "low" functions for providing high and low LED intensities respectively.

* * * * *